United States Patent [19]

Denny et al.

[11] Patent Number: 5,691,371
[45] Date of Patent: Nov. 25, 1997

[54] NITROBENZYL MUSTARD QUATERNARY SALTS AND THEIR USE AS HYPOXIA-SELECTIVE CYTOTOXIC AGENTS

[75] Inventors: William Alexander Denny; William Robert Wilson; Moana Tercel, all of Auckland, New Zealand

[73] Assignee: Auckland UniServices Limited, Auckland, New Zealand

[21] Appl. No.: 525,785

[22] PCT Filed: May 24, 1994

[86] PCT No.: PCT/NZ94/00046

§ 371 Date: Sep. 27, 1995

§ 102(e) Date: Sep. 27, 1995

[87] PCT Pub. No.: WO94/27954

PCT Pub. Date: Dec. 8, 1994

[30] Foreign Application Priority Data

May 25, 1993 [NZ] New Zealand .................. 245270

[51] Int. Cl.$^6$ .................................. A61K 31/415
[52] U.S. Cl. .................. 514/399; 548/326.5; 548/327.1; 548/327.5; 548/328.5
[58] Field of Search .................. 514/399; 548/326.5, 548/327.1, 327.5, 328.5

Primary Examiner—Matthew V. Grumbling
Assistant Examiner—Michael Bucknum
Attorney, Agent, or Firm—Young & Thompson

[57] ABSTRACT

Nitrobenzyl mustard quaternary salts of formula (I),

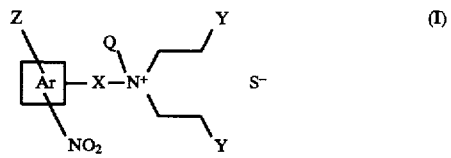

and the pharmaceutically acceptable salts thereof, process for their manufacture and their chemotherapeutic use as hypoxia selective cytotoxic agents. Wherein, X represents a linker chain —$CR_1R_2$— or $CR_1=CR_2$— (where $R_1$ and $R_2$ are separately H, lower alkyl, phenyl or nitrophenyl; Y is halogen or $OSO_2R$; Q is lower alkyl (optionaly substituted with alkyl and/or ether groups and containing up to 6 carbons) or nitrophenyl; Ar represents a mono- or bicyclic aromatic unit, R is lower alkyl optionally substituted with alkyl and/or other groups, and may contain up to eight carbon atoms. Z represents one or more of the groups $NO_2$, $SO_2R$, CONHR, R, OR, SR, $CF_3$ and aza (ring —CH= replaced by —N=); with the proviso that when H–Cl or Br, Q=Me, and $X=CH_2$— then Ar≠2-nitrophenyl or 4-nitrophenyl.

7 Claims, 3 Drawing Sheets

NITROBENZYL MUSTARD QUATERNARY SALTS AND THEIR USE AS HYPOXIA-SELECTIVE CYTOTOXIC AGENTS

FIELD

The present invention relates to novel aromatic bis(2-haloethyl) and aromatic bis(2-alkylsulfonyloxyethyl) quaternary ammonium salts which have the property of releasing cytotoxic nitrogen mustards following bioreduction. These compounds show selective cytotoxicity against hypoxic mammalian and bacterial cells. The present invention also relates to the use of these compounds as hypoxia-selective cytotoxins; reductively-activated prodrugs for cytotoxins; and/or hypoxic cell radiosensitisers and/or anti-cancer agents. The present invention also relates to novel intermediates in the preparation of the compounds of the invention.

BACKGROUND

A considerable number of chemotherapeutic agents are known. Some are administered in order to selectively destroy the neoplastic cells wherever they may be and thereby cure the cancer. It is difficult to create a highly selective cytotoxic agent, as neoplastic cells often differ only slightly from normal body cells. One difference is that cancer cells exhibit uncontrolled growth and hence divide repeatedly. However treatments intended to attack dividing cells also affect tissues in which continual cell division occurs—such as the skin and hair, blood-forming tissues, and the epithelium of the gut—even though protocols which minimise these side-effects are used. Occasionally a tumour may exhibit peculiar biochemical properties (such as Sertoli cell turnouts) and a specific chemotherapeutic agent can be devised to affect such cells. There is relatively little that can be done for the general class of solid tumours in which cell division is sparse or absent within the central regions of such tumours, because of an imperfect blood supply. While capillaries will tend to proliferate into hypoxic regions, adjacent uncontrolled growth may tend to cut off the supply to a newly set up circulation bed.

Cell populations which exist at low oxygen concentrations (i.e. hypoxic cells) in solid tumors appear to limit the effectiveness of both radiotherapy and conventional chemotherapy. However the existence of such hypoxic cells also offers a possible therapeutic opportunity, since such hypoxia is generally limited to solid tumour tissue. Drugs which could target hypoxic cells (the hypoxia-activated cytotoxins) would therefore be tumour-specific. Because the regions of severe hypoxia (<0.01% $O_2$) typically required for activation of bioreductive drugs constitute only a small proportion of most solid tumors, the activated cytotoxin should preferably be capable of diffusing for a limited distance. Hypoxia-selective cytotoxins (HSC's) have the potential to turn the hypoxic microenvironment of solid tumors to chemotherapeutic advantage.

A paper published in 1968—Papanastassiou, Z. B.; Bruni, R. J.; White, E. V. entitled Potential carcinolytic agents. VI. New deactivated biological alkylating agents. *Experientia*, 1968, 24, 325. discusses the use of certain quaternary nitrogen mustards, as deactivated biological alkylating agents. Preliminary screening against Dunning leukaemia and Walker carcinosarcoma showed some cytotoxic activity. The paper proposed activation of the compounds by thiols, with reference to diffuse tumours such as leukaemias. The paper does not suggest nor teach that these or similar compounds would be useful for releasing the cytotoxin, mechlorethamine, selectively in hypoxic conditions such as occur within solid tumours. The high selectivity of the compounds of the present invention for hypoxic cells suggests that the mechanism is not activated by nucleophilic displacement by thiols, as was originally proposed. In fact, the compounds of the present invention proved surprisingly stable in the presence of thiols.

STATEMENT OF THE INVENTION

In one aspect, the present invention comprises novel compounds of formula (I) and their pharmaceutically acceptable addition salts.

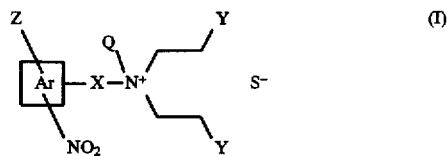

Wherein, X represents a linker chain —$CR_1R_2$— or $CR_1$=$CR_2$— (where $R_1$ and $R_2$ are separately H, lower alkyl, phenyl or nitrophenyl; Y is halogen or $OSO_2R$; Q is lower alkyl (optionally substituted with alkyl and/or ether functions and containing up to 6 carbons) or nitrophenyl; Ar represents a mono- or bicyclic aromatic unit, examples of which (Ia–Ih) are listed below; R is lower alkyl optionally substituted with alkyl and/or ether groups, and may contain up to eight carbon atoms, Z represents one or more of the groups $NO_2$, $SO_2R$, $CONHR$, R, $OR$, $SR$, $CF_3$ and aza (ring —CH— replaced by —N=);

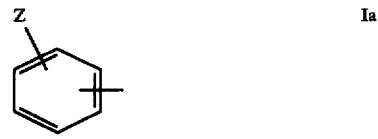

Ia

Ib

Ic

Id

Ie

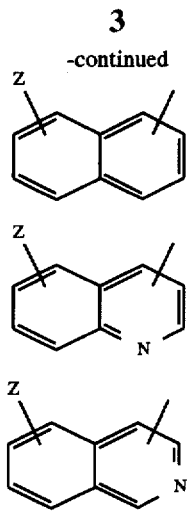

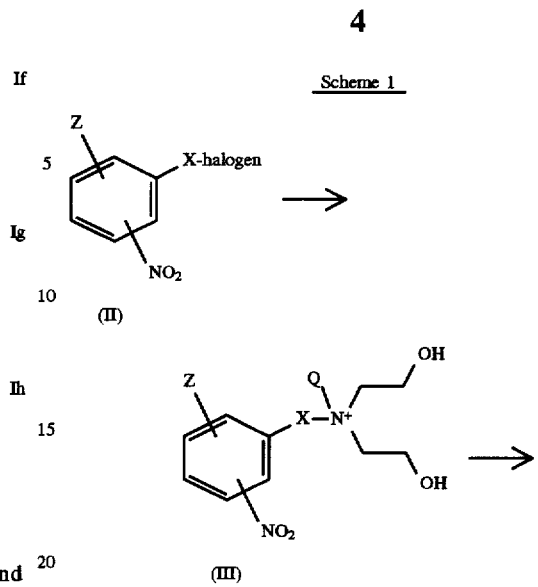

Scheme 1 with the proviso that when Y=Cl or Br, Q=Me, and X=—CH₂—then Ar≠2-nitrophenyl or 4-nitrophenyl.

Preferred compounds of Formula 1 are:

N-Bis(2-chloropropyl)-N-methyl-N-(2-nitrobenzyl) ammonium chloride;

N,N-Bis(2-chloroethyl)-N-methyl-N-(3-nitrobenzyl) ammonium chloride;

N-Bis(2-chloroethyl)-N-methyl-N-(3-methyl-2-nitrobenzyl)ammonium chloride;

N,N-Bis(2-chloroethyl)-N-methyl-N-(4-methyl-2-nitrobenzyl)ammonium chloride;

N-Bis(2-chloroethyl)-N-methyl-N-(5-methyl-2-nitrobenzyl)ammonium chloride;

N-Bis(2-chloroethyl)-N-(3-methoxy-2-nitrobenzyl)-N-methylammonium chloride;

N,N-Bis(2-chloroethyl)-N-(4-methoxy-2-nitrobenzyl)-N-methylammonium chloride;

N-Bis(2-chloroethyl)-N-(5-methoxy-2-nitrobenzyl)-N-methylammonium chloride;

N-Bis(2-chloroethyl)-N-(3,5-dinitrobenzyl)-N-methylammonium chloride;

N-Bis(2-chloroethyl)-N-methyl-N-[(4-methylsulfonyl)benzyl]ammonium chloride;

N-Bis(2-chloroethyl)-N-methyl-N-[(5-nitro-1-naphthyl)methyl]ammonium chloride;

N-Bis(2-chloroethyl)-N-methyl-N-[(a-nitro-1-naphthyl)methyl]ammonium chloride;

N-Bis(2-chloroethyl)-N-methyl-N-[(1-methyl-4-nitro-5-imidazolyl)methyl]ammonium chloride;

and their pharmaceutically acceptable salts.

The compounds of formula (I) can be prepared by the methods outlined in Scheme 1 below. Reaction of appropriate aromatic a-methyl halides (II) with N-alkyl- or N-aryldiethanolamines gives the novel quaternary diols (III), which can be converted to the desired quaternary mustards (I) of Table 2 by treatment with SOCl₂ at room temperature for prolonged times.

The quaternary diols of the general formula III:

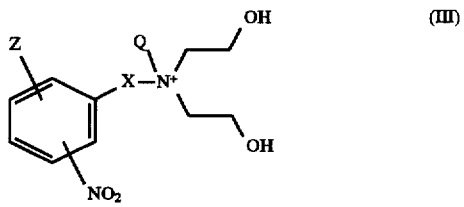

wherein Z, X and Q have the meanings given above without the proviso, are novel intermediates. The present invention also relates to the use of the compounds of formula I, without the proviso, as hypoxia-selective cytotoxins. Their formulation as reductively activated prodrugs can be done by conventional means. It has been found that cytotoxins can act beneficially when used in conjunction with radiotherapy, or they can be used alone as anticancer agents.

The present invention will be further understood from the following detailed description of a preferred embodiment, given by way of example only, with reference to the accompanying drawings in which:

FIG. 1 shows the fragmentation of N-bis(2-chloroethyl)-N'-methyl-N-(2-nitrobenzyl) ammonium chloride [compound(1)] to release mechlorethamine following one-electron reduction.

FIG. 2 shows oxygen dependence of cell killing by compound (1). EMT6 cells were treated with the drug at 2 mM for 3 hours under a range of gas phases containing 5% CO₂ and 0–95% O2. O2 concentrations were measured with a sensitive O2 electrode.

Figure 1:
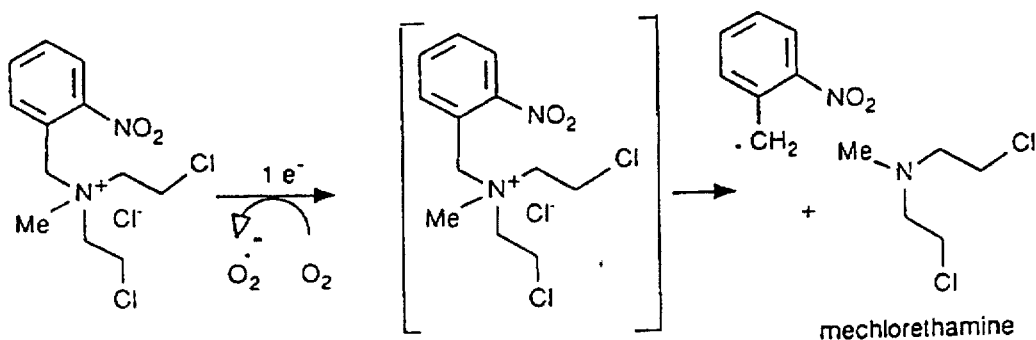
Figure 2:
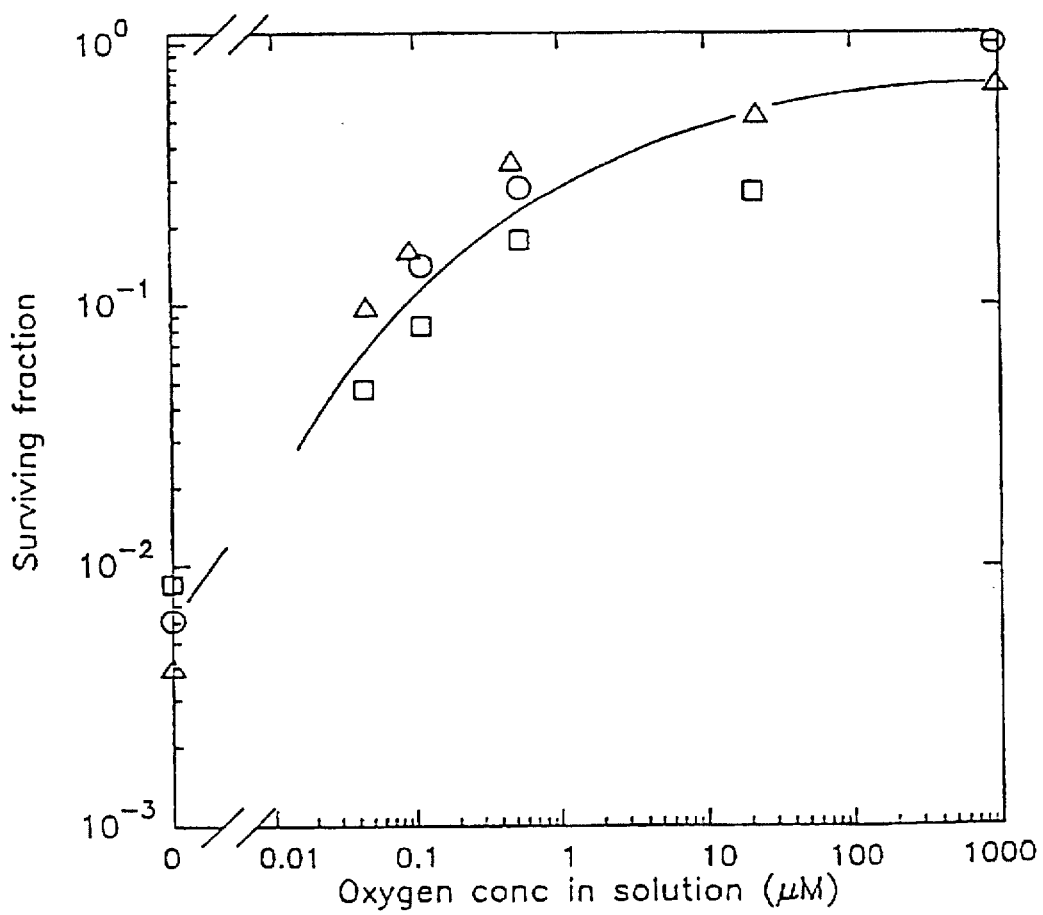

Nitrobenzyl mustard quaternary salts are a new class of HSCs which show very high hypoxic selectivities in vitro. The compounds in Table 1 were designed to undergo fragmentation of the radical anion 1 formed on (oxygen-inhibitable) one-electron reduction of the nitro group, to release the aliphatic nitrogen mustard mechlorethamine (FIG. 1).

Given that many solid tumours have hypoxic tissue within them which is an unusual state within the body, these compounds can form a target-selective drug with the advantage over many known compounds used in conventional. Irradiation or treatment with drugs adversely affecting tumour perfusion rates may enhance the hypoxic state and thereby enhance the activities of these compounds.

The one-electron reduction of nitroaromatic compounds by cellular enzymes to give the vitro radical anions is controlled primarily by the reduction potential of the compound, and can occur in both oxygenated and hypoxic cells. In the former, reoxidation by molecular oxygen can regenerate the parent compound. However, in the absence of oxygen, fragmentation of the initial radical anion can occur generating, from compound 1, a benzyl radical and releasing the reactive nitrogen mustard mechlorethamine. FIG. 1 shows the fragmentation of compound 1 to release mechlorethamine following one-electron reduction. This proposed mechanism is supported by much published evidence that closely related nitrobenzyl halides and nitrobenzyl quaternary ammonium salts do fragment following one electron reduction, and that the nitro radical anions derived from such compounds are readily reoxidised by oxygen in vitro.

This design for HSCs has a number of advantages. The cationic charge on the quaternary salt ensures a high degree of deactivation of the mustard and excellent water solubility for the compound. The large positive Hammett substituent parameter ($\sigma o,p$) of the benzyl quaternary function (expected to be similar to the value of +0.67 reported for $CH_2N^+(Me)_3$) equates to a calculated reduction potential of −330 mV for the 4-isomer (compound 5), while cyclic voltammetry measurements indicate a value of approximately −350 reV. These estimates fall within the window (−300 to −450 mV) suggested as desirable for HSCs.

Mechlorethamine not only shows activity against non-cycling cells, but has a half life sufficiently long (ca. 15 min) that it would be expected to back-diffuse to surrounding tumor cells at higher oxygen concentration. The rates of the fragmentation reaction can be controlled over several orders of magnitude by appropriate structural changes (in a series of nitrobenzyl halides), allowing in principle for this fragmentation to be competitive with the back-oxidation process at particular oxygen concentrations.

The rate of release of mechlorethamine from the compound in the presence of cells under aerobic and hypoxic conditions was determined by trapping the released mustard with diethyldithiocarbamate, and measuring the bisadduct by high-performance liquid chromatography (HPLC)—see "Reduction of nitromin to nitrogen mustard; unscheduled DNA synthesis in aerobic or anaerobic rat hepatocytes, JB1, BL8 and Walker carcinoma cell lines". Carcinogenesis 10:2113–2118;1989).

Diethyldithiocarbamate (100 mL of a 27.5 mM solution in 0.95 M HEPES buffer) was added to 1 mL aliquots of EMT6 cell suspensions previously treated with the quaternary mustard 1 (at 1 mM) for 3 hr. The resulting mixtures were incubated at 37° C. for 15 min to allow derivatization of free mechlorethamine, then diluted with ice-cold methanol (9 mL) (to precipitate protein) and centrifuged. Supernatants were dried under reduced pressure and redissolved in 70% MeOH for HPLC analysis on a Waters C18 mBondapak 8×100 mm column, beginning with a 25:75 ratio of solvents A & B (A=80% MeCN/20% water; B=0.5 M formate buffer, pH 4.5), followed by a linear gradient to a ratio of 90:10 A/B. Products p3 and p4 (as seen in Table 3) were detected by absorbance at 280 nm, and their identity confirmed by injection of authentic synthetic samples. A calibration curve for recovery of p4 from cell suspensions was constructed from samples taken from an aerobic suspension of EMT6 cells (1×106 cells/mL) treated with known amounts of mechlorethamine, then sampled (after 3 min) as above. This gave a linear plot over two orders of magnitude, best fitted by the line y=1.41x+0.06 (r=0.999), where y=actual (added) mechlorethamine concentration; x=recovered (measured) concentration (as bisadduct p4). Because the half life of mechlorethamine under these conditions is ca. 70 min (measured by biosassay) errors due to mechlorethamine breakdown are small.

The cationic charge on compound 1 confers high water-solubility (>400 mM at 20° C.). The large positive Hammett substituent parameter ($\sigma$=0.67) of the benzyl quaternary function also ensures an unusually high nitro group reduction potential for a nitrobenzene derivative (−369 mV as determined by pulse radiolysis, using benzyl viologen as standard) bringing it into the appropriate range for efficient cellular reduction.

Table 1 shows amounts of mechlorethamine (detected as its dithiocarbamate adduct p4) released from cell cultures following a 3 hr exposure of EMT6 cells to 1 mM of compound 1.

TABLE 1

| Conditions (cells/ml) | n[a] | p3 (nM)[b] | p4 (nM)[b] | p2 (mM)[c] | yield[d] |
|---|---|---|---|---|---|
| oxic, 10⁶ cells/mL | 6 | 3.9 ± 0.6 | 0.37 ± 0.02[e] | 0.58 | (0) |
| hypoxic, 10⁶ cell/mL | 6 | 2.6 ± 0.4 | 1.12 ± 0.3 | 1.6 | 0.1% |
| hypoxic, 5 × 10⁶ cell/mL | 3 | 3.1 ± 0.3 | 7.39 ± 0.02 | 10.5 | 15 |

[a]Number of determinations.
[b]Amounts measured in 1 ml samples, ± SEM.
[c]Concentration of mechlorethamine (p2) in the initial cell suspension, determined from the previous column by use of the calibration curve y = 1.4x + 0.06.
[d]Observed approximate yield of p2 from compound 1 calculated using 0.58 mM as an average "background" level of p2 and assuming a constant concentration of 1000 mM of the parent drug.
[e]Lower concentration than that of p3 because the mechlorethamine concomitantly released during the 15 min analysis time has not completely reacted with the derivatizing reagent diethyldithiocarbamate (DDC).

The ability of the drug to release mechlorethamine following cellular reduction was studied using derivatization with diethyldithiocarbamate. This reagent reacts rapidly with mechlorethamine to give the bis(dithiocarbamate) p4, and has been used previously to study the reductively-activated release of the related compound nor-nitrogen mustard from nitromin. In the present case the analysis is complicated by the fact that, while diethyldithiocarbamate does not react directly with the deactivated quaternary mustard, it does slowly displace mechlorethamine from it by nucleophilic substitution to give the benzyl dithiocarbamate p3. The mechlorethamine released by this reaction then reacts with diethyldithiocarbamate to give further adduct p4.

This is seen from Table 1, where a roughly constant mount of the benzyl dithiocarbamate p3 (ca. 3 mM; 0.3% of the concentration of quaternary mustard present) is detected under all conditions. This arises by the direct substitution pathway during the 15 rain incubation. The small mount of mechlorethamine adduct p4 detected after a 3 hr exposure of oxygenated EMT6 cells to the drug is attributed to subsequent reaction of the mechlorethamine released by this reaction. The level of this is much lower than that of p3, since the mechlorethamine is released over the entire 15 min incubation period, and the derivatization reaction is not instantaneous; thus not all is derivatized. Under hypoxic conditions, while the level of p3 remains the same, increasing mounts of mechlorethamine adduct p4 are detected (greater with higher cell density); the additional amounts are attributed to direct release of mechlorethamine following cellular one-electron reduction (see FIG. 1).

However, if the level measured under aerobic conditions is regarded as "background", the data of Table 3 indicate an increasing yield (rate of release) of mechlorethamine under hypoxic conditions, generated via path B (0.1% of the concentration of quaternary mustard present with 106 cells/mL, 1% with 5 x 106 cells/mL).

The cytotoxicity and hypoxic selectivity of compounds 1, 4 and 5 have been evaluated in cultures of Chinese hamster ovary cells (Table 4). Growth inhibition assays were performed as described in detail in W. R. Wilson, R. F. Anderson and W. A. Denny. J. Med. Chem., 1989, 32, 23; G. J. Finlay, B. C. Baguley and W. R. Wilson. Anal. Biochem., 1984, 139, 172, (the contents of which are hereby imported by way of reference)

The reduction potential of compound 5 is calculated as ca. $-330$ mV, using the empirical equation $E(1)$ $(mV)=163sp--492$, and estimating sp- for $CH2N+CH3(CH2CH2Cl)2$ as ca 1.0 from the known value of sp for $CH2N+(CH3)3$ of 0.67 Hansch, C.; Leo, A. J. Substituent Constants for Correlation Analysis in Chemistry and Biology; Wiley and Sons Ltd: New York, 1979.).

Compound 4 showed by far the lowest cytotoxicity, using either the AA8 subline in growth inhibition assays or the UV4 cell line in clonogenic assays. The greater potencies of compounds 1 and 5 support the proposed mechanism of action, since the radical anions of 3-nitrobenzyl halides are known to fragment more than 103 times more slowly than the 2- or 4-nitro isomers. The release of mechlorethamine from compound 1 following incubation with hypoxic EMT6 cells has been confirmed by trapping the released mustard with diethyl dithiocarbamate, and HPLC analysis of the adduct.

Figure 4:
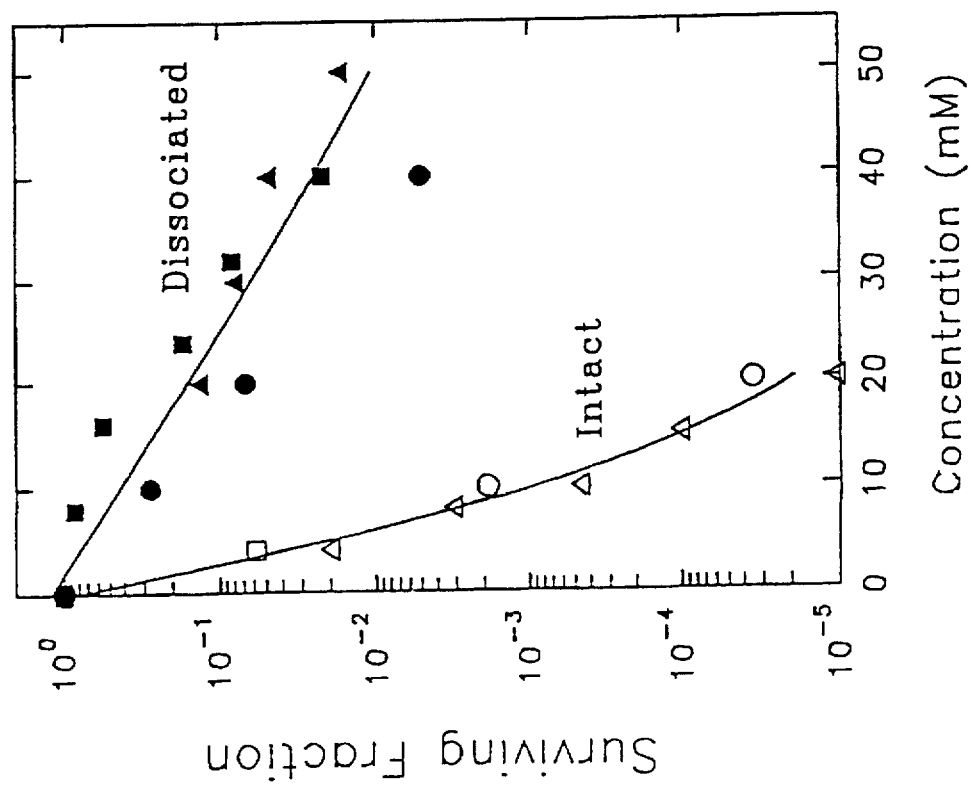
FIG. 4 shows cell survival after treatment of intact (open symbols) and dissociated (closed symbols) EMT6 spheroids with compound (1) for 1 h under aerobic conditions.

The selectivity of compound 1 for hypoxic cells was also assessed by determining clonogenic survival after exposure for 1 hr in stirred suspensions of UV4 cells gassed continuously with 5% $CO2$ or $N2$ (FIG. 4). The concentration of compound 1 required to reduce survival to 10% of controls (C10) was 200-fold less under hypoxic than aerobic conditions, showing compound 1 to be one of the most hypoxia-selective mono-bioreductive agents yet reported. This property is not restricted to repair-deficient cell lines, since recent studies show that the compound has pronounced hypoxic selectivity (>100-fold) with EMT6 mouse mammary carcinoma cells in similar assays, although mechlorethamine itself shows no significant selectivity with these cells. The marked difference in hypoxic selectivity between compounds 1 and 4 could also be due to different rates of fragmentation (the half life of the radical anion derived from 2-nitrobenzyl chloride is about half that derived from the 3-isomer), or to differences in rates of enzymic reduction.

Stirred suspension culture assays using magnetically-stirred 10 mL suspension cultures (late log phase UV4 cells, 106/mL) were performed by removing samples periodically during continuous gassing with 5% $CO_2$ in air or $N_2$. Both cell suspensions and drug solutions in growth medium were pre-equilibrated under the appropriate gas phase for 60 min prior to mixing, to ensure essentially complete anoxia throughout the period of drug contact in hypoxic cultures. Several drug concentrations were investigated to identify those concentrations which gave, under both aerobic and hypoxic conditions, approximately the same rate of cell kill. The ratios of the concentration×time for a surviving fraction of 10% ($CT_{10}$) for these two survival curves was used as the measure of hypoxic selectivity.

The UV4 cell line, which is defective in DNA crosslink repair, is hypersensitive to DNA cross-linking agents, as shown by the HF value (ratio of $IC_{50}$ values in the wild-type AA8 and UV4 lines) of 28 for mechlorethamine (Table 2). The high HF values also shown by compounds 1 and 5 suggest that the mechanism of toxicity may be by crosslinking. The fact that these HF values are much higher than that of mechlorethamine (a typical crosslinking agent) may be due to limited cellular uptake of these fully-cationic compounds (possibly by a saturable, transport-mediated process). This would serve to exaggerate the ratio, since very high extracellular drug levels might be needed to attain a cytotoxic intracellular concentration in the repair-competent cells. Studies of drug uptake of these compounds are in progress.

Cytotoxicity to EMT6 cells.

Figure 3:
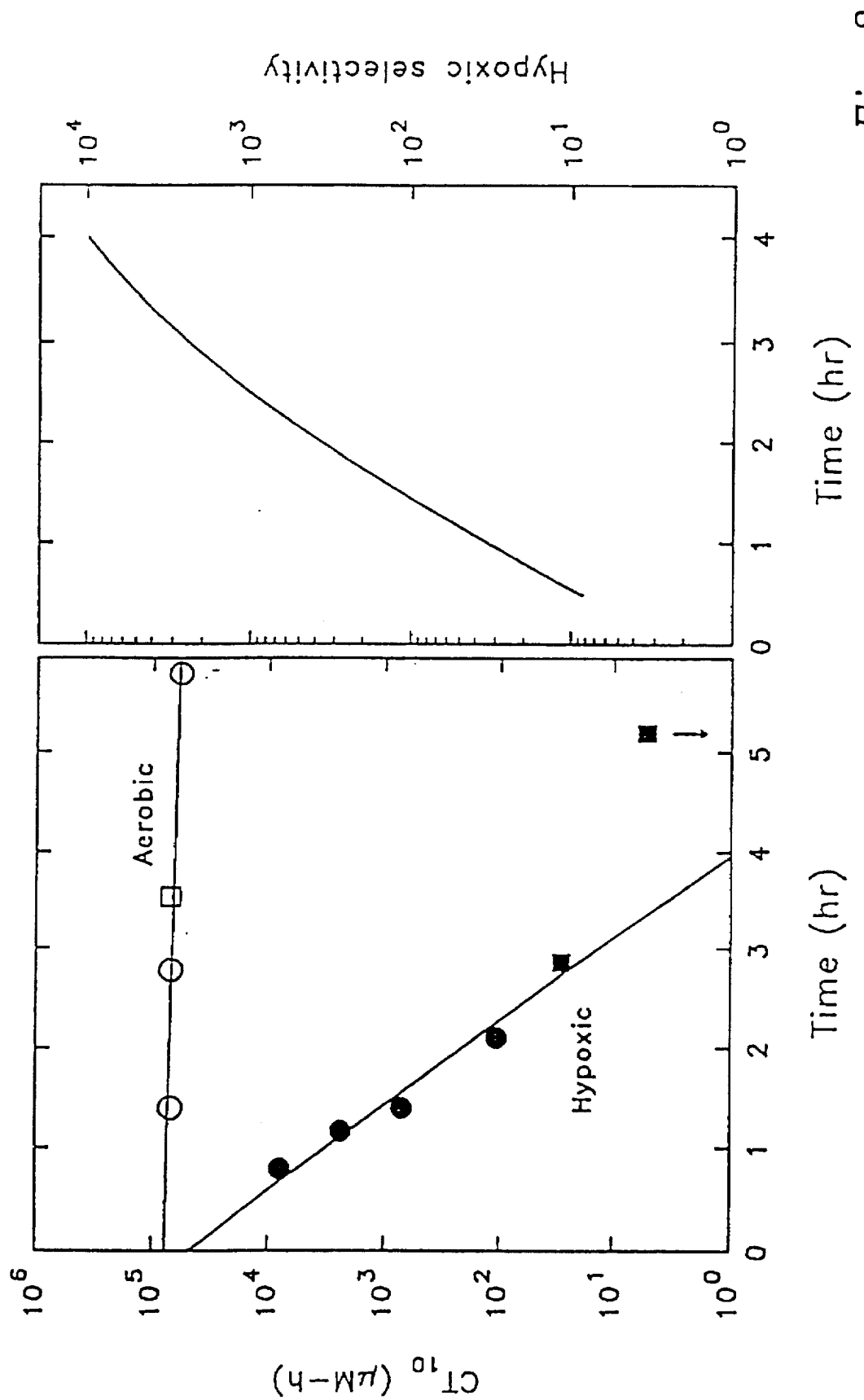
FIG. 3 shows drug concentration×time for 10% survival (CT10) verus time in aerobic (open symbols) and hypoxic (filled symbols) EMT6 single cell suspensions.

We have also observed that compound 1 shows high selectivity (approximately 200-fold following a 1-hr exposure) for hypoxic EMT6 cells (mouse mammary carcinoma). While lower selectivity is seen after 1 hr in the cross-link repair competent cell line EMT6 compared with UV4, the differential increases markedly with time, reaching several thousand-fold after 4 hr. The cytotoxicity of the compound 1 to stirred suspensions of aerobic and hypoxic cultures of EMT6 cells was measured by clonogenic assay, using as a measure of potency the concentration×time for 10% survival (CT10). This is illustrated in FIG. 3. Where different symbols indicate separate experiments. Hypoxic selectivity was determined as the ratio of aerobic and hypoxic CT10 values at each time. Multicellular EMT6 spheroids (average diameter 1200 mm) were treated with compound 1 for 1 hr at 37° C. in well-stirred cultures equilibrated with 20% $O_2$, either immediately before or immediately after dissociation (pronase 0.5 mg/mL, DNAase 0.2 mg/mL), and the resulting single cell suspensions were analyzed as above.

Experiments with EMT6 spheroids show that intact spheroids are much more sensitive to the drug than are cells from dissociated spheroids, when exposed under otherwise identical conditions (FIG. 4), supporting the "hypoxia plus local diffusion" concept. FIG. 4 shows cell survival after treatment of intact (open symbols) or dissociated (filled symbols) EMT6 spheroids with N,N-bis(2-chloroethyl)-N-methyl-N-(2-nitrobenzyl)ammonium chloride for 60 min under aerobic conditions. Different symbols again indicate separate experiments.

This is in contrast to results for known activated nitrogen mustards such as N,N-bis(2-chloroethyl)-4-aminoaniline, which shows similar activity in both intact and dissociated spheroids, and supports the view that reductive activation of the quaternary mustard occurs in hypoxic regions of the spheroid, releasing mechlorethamine which can back-diffuse to kill surrounding oxygenated cells. The experiments with EMT6 spheroids provide evidence that the drug does act as a hypoxia-selective prodrug of a diffusible cytotoxin. Its greatly enhanced activity against intact spheroids cannot be explained solely by preferential killing of the small proportion of hypoxic cells they contain, and is evidence for release of a diffusible cytotoxin (mechlorethamine) which can kill considerable numbers of surrounding cells at higher levels of oxygenation. The alternative possibility, that the drug is activated efficiently at quite high oxygen tensions which may occur in a large proportion of the spheroid cells is unlikely, since preliminary experiments indicate a low K value (<0.1% O2) in EMT6 cell suspensions. It showed only marginal in vivo activity as a radiosensitiser or an hypoxia-selective cytotoxin when given as a single dose. However, the marked time dependence of killing of hypoxic cells suggests that multiple dosing, to provide lower concentrations of drug for longer times, may be more appropriate.

Compound 1 in vivo trials with KHT tumours.

Figure 5:
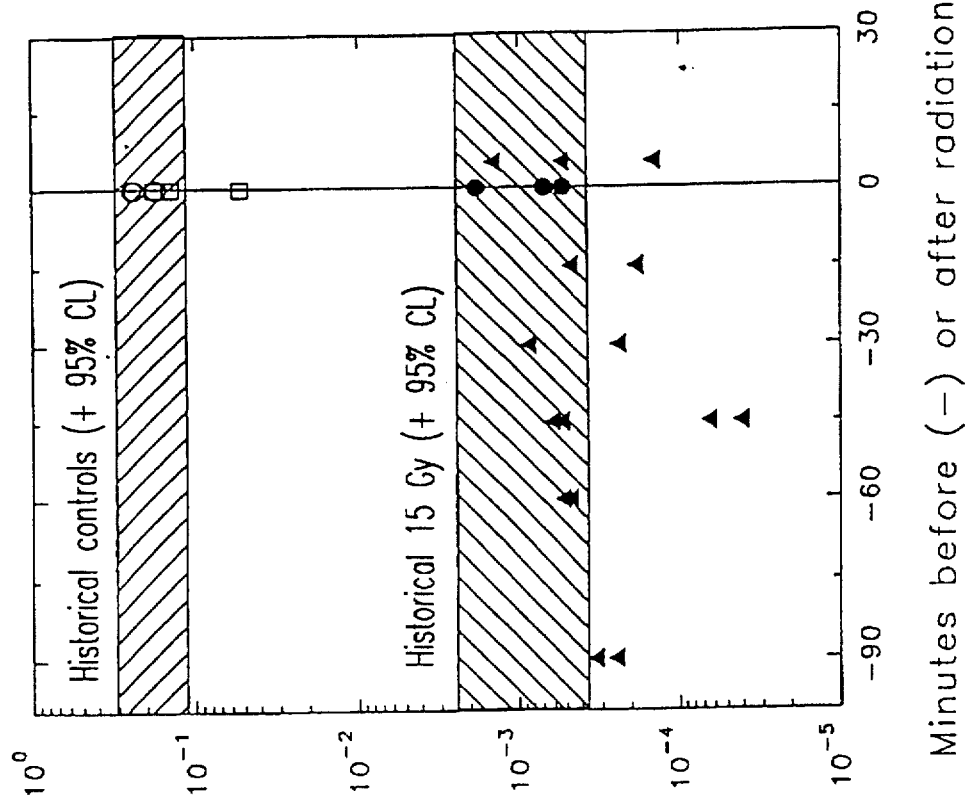
FIG. 5 shows evaluation of compound (1) against the KHT tumor in mice.

In vivo activity was evaluated in mice beating subcutaneous KHT tumors. The drug was administered intraperitoneally as a single dose at 75 mmol/kg (75% of the maximum tolerated dose) at varying times before and after irradiation (15 Gy). Tumors were excised after 14 hr, and cell survival was determined by clonogenic assay. When administered at 75% of the maximum tolerated dose, it showed only weak activity against the KHT tumor in combination with radiation, although this activity (when comparing all times with radiation alone) was statistically significant (FIG. 5). This figure details evaluation of compound 1 against KHT tumors in mice. A single dose of drug (75 mmol/kg) was administered intraperitoneally at the indicated times before or after irradiation (15 Gy). Each point is from 3-4 pooled tumors. Symbols represent control (○); drug only (□); radiation only (●); radiation plus drug (▲). Data are from four separate experiments. Hatching represents cell survival (±95% confidence level) of historical controls: top, without drug or irradiation; bottom, irradiation alone.

These compounds and in particular compound 1 show very high selectivity for hypoxic EMT6 cells in culture, rising to several thousand-fold after 4 hr, and compound 1 is thus one of the most hypoxia-selective agents reported in mammalian cells in culture. The reason for the unusual time dependence of hypoxic selectivity is not known, but may be due in part to the slow kinetics of release and subsequent accumulation of mechlorethamine in hypoxic cultures.

Further chemical development and in vivo biological studies of compounds of this class are in progress.

The following compounds are examples of the present invention prepared by the method of Scheme 1. The structures and physiochemical properties of these compounds are given in Table 2 and their biological activity in cell culture (specify) are given in Table 3.

TABLE 2

Structure and physicochemical properties of certain nitrobenzyl quaternary mustards

| No. | $R_1$ | $R_2$ | $R_3$ | X | Y | yield (%) | mp (°C.) | solvent[a] | formula | analyses[b] |
|---|---|---|---|---|---|---|---|---|---|---|
| 1 | 2-$NO_2$ | H | H | Cl | Cl | 87 | 152–153.5 | A | $C_{12}H_{17}Cl_3N_2O_2$ | C, H, N, Cl |
| 2 | 2-$NO_2$ | H | H | Br | Br | 15 | 150–155 | C | $C_{12}H_{17}Br_3N_2O_2$ | C, H, N, Br |
| 3 | 2-$NO_2$ | H | Me | Cl | Cl | 50 | 147–148 | B | $C_{14}H_{21}Cl_3N_2O_2 \cdot H_2O$ | C, H, N |
| 4 | 3-$NO_2$ | H | H | Cl | Cl | 92 | 157–158 | A | $C_{12}H_{17}Cl_3N_2O_2 \cdot H_2O$ | C, H, N |
| 5 | 4-$NO_2$ | H | H | Cl | Cl | 45 | 175–177 | A | $C_{12}H_{17}Cl_3N_2O_2$ | C, H, N, Cl |
| 6 | 2-$NO_2$ | 3-Me | H | Cl | Cl | 66 | 167–168 | D | $C_{13}H_{19}Cl_3N_2O_2$ | C, H, N |
| 7 | 2-$NO_2$ | 4-Me | H | Cl | Cl | 73 | 151–152 | D | $C_{13}H_{19}Cl_3N_2O_2$ | C, H, N, Cl |
| 8 | 2-$NO_2$ | 5-Me | H | Cl | Cl | 51 | 133–134 | E | $C_{13}H_{19}Cl_3N_2O_2$ | C, H, N, Cl |
| 9 | 2-$NO_2$ | 3-OMe | H | Cl | Cl | 72 | 175–176 | D | $C_{13}H_{19}Cl_3N_2O_3$ | C, H, N |
| 10 | 2-$NO_2$ | 4-OMe | H | Cl | Cl | 34 | 142–143 | F | $C_{13}H_{19}Cl_3N_2O_3$ | C, H, N, Cl |
| 11 | 2-$NO_2$ | 5-OMe | H | Cl | Cl | 47 | 126–127 | F | $C_{13}H_{19}Cl_3N_2O_3 \cdot 0.5H_2O$ | C, H, N |
| 12 | 3-$NO_2$ | 5-$NO_2$ | H | Cl | Cl | 84 | 201–202 | G | $C_{12}H_{16}Cl_3N_3O_4$ | C, H, N, Cl |
| 13 | 4-$SO_2$Me | H | H | Cl | Cl | 55 | 179–180 | C | $C_{13}H_{20}Cl_3NO_2S \cdot 05H_2O$ | C, H, N |
| 14 | 5-$NO_2$ | | | | | 64 | 152–153.5 | B | $C_{16}H_{19}Cl_3N_2O_2$ | C, H, N, Cl |
| 15 | 8-$NO_2$ | | | | | 37 | 103–104 | H | $C_{16}H_{19}Cl_3N_2O_2 \cdot H_2O$ | C, H, N, Cl |
| 16 | | | | | | 66 | 173–176 | I | $C_{10}H_{17}Cl_3N_4O_2$ | C, H, N, Cl |

Footnotes for Table 2
[a]Recrystallisation solvent: A, EtOH—$Et_2O$; B, iPrOH—$Et_2O$; C, EtOH-iPrOH; D, iPrOH; E, $CH_3CN$; F, iPrOH—EtOAc; G, EtOH; H, $Me_2Co$; I, MeOH.
[b]Analytical results within ± 0.4% of the theoretical value.

TABLE 3

Biological activity of the nitroaromatic quaternary mustards of Table 2 i cell culture.

| | Growth inhibition | | | | Clonogenic assay | |
|---|---|---|---|---|---|---|
| | $IC_{50}$ (mM)[a] | | hypersensitivity factor[b] | | hypoxic $CT_{10}$ [c] | air/$N_2$[d] |
| no. | AA8 | UV4 | EMT6 | FME | (mH-h) | ratio |
| 1 | 2695 ± 1305 | 305 ± 72.5 | 40.1 ± 11.6 | 23.5 ± 8.38 | 60,000 | 3000 |
| 2 | 14640 ± 2485 | 17 ± 7.05 | 17.1 ± 1.99 | 55.9 ± 12.7 | 24,000 | 37 |
| 3 | 14800 ± 1503 | 2.58 ± 0.194 | 11.1 ± 1.59 | 118 ± 27.1 | 29250 | 6.5 |
| 4 | 20938 ± 2808 | 94.6 ± 83.9 | 16.0 ± 2.56 | 71.5 ± 47.8 | >50,000 | — |
| 5 | 6143 ± 1678 | 2943 ± 810 | 121 ± 31.4 | 22.2 ± 3.26 | 6000 | 8–94 |
| 6 | 2999 ± 1163 | 734 ± 113 | 398 ± 197 | 327 ± 81.0 | ca. 3000 | <40 |

TABLE 3-continued

Biological activity of the nitroaromatic quaternary mustards of Table 2 i cell culture.

| | Growth inhibition | | | | Clonogenic assay | |
|---|---|---|---|---|---|---|
| | $IC_{50}$ (mM)[a] | | hypersensitivity factor[b] | | hypoxic $CT_{10}$ [c] | air/$N_2$[d] |
| no. | AA8 | UV4 | EMT6 | FME | (mH-h) | ratio |
| 7 | 3304 ± 876 | 469 ± 67.5 | 120 ± 45.2 | 54.2 ± 1.93 | 870 | 240 |
| 8 | 689 ± 37.4 | 205 ± 9.3 | 68.1 ± 16.4 | 19.3 ± 11.9 | 390 | 10 |
| 9 | 10509 ± 3155 | 1560 | 58.1 ± 37.0 | 31.7 ± 7.23 | 3200 | 4.8 |
| 10 | 7759 ± 132 | 435 ± 56.4 | 53.6 ± 16.9 | 26.5 | 23500 | 7000 |
| 11 | 8813 ± 2211 | 297 ± 160 | 44.5 ± 14.5 | 26.3 ± 2.07 | 10,000 | 9.1 |
| 12 | 129 ± 53.4 | 530 ± 84.6 | 41.3 ± 7.89 | 64.8 ± 49.3 | 29200 | 37 |
| 13 | 13539 ± 1174 | 195 ± 23.1 | 90.6 ± 9.6 | 26.2 ± 6.96 | >90,000 | — |
| 14 | 5248 ± 486 | 14.4 ± 6.06 | 11.7 ± 5.02 | 7.60 ± 1.71 | 9600 | 1 |
| 15 | 1383 ± 100 | 36.6 ± 5.66 | 12.0 ± 6.98 | 16.3 ± 7.61 | 2100 | <2.6 |
| 16 | 324 ± 133 | 117 ± 13.9 | 24.5 ± 6.29 | 14.8 ± 6.20 | 300 | 100 |
| M | 2.2 ± 0.01 | 28 ± 8 | | | | |

Footnotes for Table 3
[a]Growth inhibition assay. $IC_{50}$ = concentration of drug (mM) for 50% inhibition of growth of AA8 cells, under aerobic conditions, 18 hr exposure.
[b]HF (hypersensitivity factor) = IC(AA8)/IC(UV4).
[c]Clonogenic assay, using stirred suspensions of UV4 cells. $C_{10}$ = concentration of drug (mM) to give 10% cell survival, under aerobic conditions, 1 hr exposure.
[d]ratio = $C_{10}$ (aerobic)/$C_{10}$ (hypoxic) for UV4 cells.
M = mechlorethamine.

COMPOUND 1

N,N-Bis(2-chloroethyl)-N-methyl-N-(2-nitrobenzyl) ammonium chloride (1). A solution of 2-nitrobenzyl chloride (5.00 g, 29 mmol) and N-methyldiethanolamine (3.47 g, 29 mmol) in $CH_3CN$ (100 mL) was heated under reflux for 6 h. The resulting red suspension was allowed to cool to 20° C., diluted with $Et_2O$ (150 mL), and stirred overnight. The resulting precipitate was filtered off and dried to give the diol N,N-bis(2-hydroxyethyl)-N-methyl-N-(2-nitrobenzyl) ammonium chloride (6.52 g, 77%). A sample was crystallised from $EtOH/Et_2O$ as plates, and analysed mp 148°–149° C. $^1H$ NMR [$(CD_3)_2SO$] δ 8.16 (dd, J=7.9, 1.5 Hz, 1 H, H-3 or H-6), 8.03 (dd, J=7.6, 1.4 Hz, 1H, H-3 or H-6), 7.90 (td, J=7.5, 1.5 Hz, 1 H, H-4 or H-5), 7.85 (dd, J=7.7, 1.5 Hz, 1H, H-4 or H-5), 5.59 (t, J=5.0 Hz, 2H, 2×OH), 5.15 (s, 2 H, $ArCH_2N$), 3.94–3.83 (m, 4H, $NCH_2CH_2O$), 3.69–3.61 (m, 2H, $NCH_2CH_2O$), 3.45–3.37 (m, 2 H, $NCH_2CH_2O$), 3.01 (s, 3H, $NCH_3$); $^{13}C$ NMR [$(CD_3)_2SO$] δ 151.0 (C-2), 136.5, 133.7, 132.2, 125.7 (C-3,4,5,6), 121.2 (C-1), 63.5, 61.5 ($ArCH_2NCH_2$), 54.9 ($CH_2OH$), 47.8 ($NCH_3$). Anal. ($C_{12}H_{19}ClN_2O_4$) C,H,N,Cl The above diol (3.00 g, 10.3 mmol) was added in portions to $SOCl_2$ (15 mL) with stirring, and the resulting pale yellow solution stirred at 20° C. with protection from moisture for 3 days. The excess $SOCl_2$ was evaporated at 20° C., and the resulting pale yellow solid recrystallized from $EtOH/Et_2O$ to give N,N-bis(2-chloroethyl)-N-methyl-N-(2-nitrobenzyl) ammonium chloride (1) as pale yellow needles (2.95 g, 87%), mp 152°–153.5° C. $^1H$ NMR [$(CD_3)_2SO$] δ 8.18 (dd, J=7.9, 13 Hz, 1H, H-3 or H-6), 8.03 (d, J=7.5 Hz, 1H, H-3 or H-6), 7.92 (td, J=7.5, 1.2 Hzs, 1 H, H-4 or H-5), 7.87 (td, J=7.7, 1.2 Hz, 1 H, H-4 or H-5), 5.19 (s, 2H, $ArCH_2N$), 4.25–4.10 (m, 4H, $NCH_2CH_2Cl$), 3.99–3.90 (m, 2H, $NCH_2CH_2Cl$), 3.81–3.73 (m, 2H, $NCH_2CH_2Cl$), 3.13 (s, 3H, $NCH_3$); $^{13}C$ NMR [$(CD_3)_2SO$] δ 150.9 (C-2), 136.6, 133.8, 132.6, 126.0 (C-3,4,5,6), 120.4 (C-1), 61.5, 61.1 ($ArCH_2NCH_2$), 47.1 ($NCH_3$), 36.0 ($CH_2Cl$). Anal. ($C_{12}H_{17}Cl_3N_2O_2$) C,H,N,Cl.

COMPOUND 2

N,N-Bis(2-bromoethyl)-N-methyl-N-(2-nitrobenzyl) ammonium bromide (2) was prepared by similar reaction to compound 1. The diol N,N-bis(2-hydroxyethyl)-N-methyl-N-(2-nitrobenzyl)ammonium bromide (pale yellow plates, mp 152°–153° C. (a known compound) was reacted with $SOBr_2$ at 40° C. for 6 days to give N,N-bis(2-bromoethyl)-N-methyl-N-(2-nitrobenzyl)ammonium bromide (2) as pale yellow prisms (15%): mp 150°–155° C. (after two recrystallizations from $EtOH/^iPrOH$, dec.); $^1H$ NMR [$(CD_3)_2SO$] δ 8.18 (d, J=8.2 Hz, 1H, H-3), 7.96–7.85 (m, 3H, H-4,5,6), 5.08 (s, 2H, $ArCH_2N$), 3.99–3.85 (m, 6H, $NCH_2CH_2Br$), 3.80–3.72 (m, 2H, $NCH_2CH_2Br$), 3.06 (s, 3H, $NCH_3$); $^{13}C$ NMR [$(CD_3)_2SO$] δ 150.9 (C-2), 136.3, 133.7, 132.6, 125.9, 120.3 (C-1,3,4,5,6), 61.0, 60.7 ($ArCH_2NCH_2$), 46.4 ($NCH_3$), 22.4 ($CH_2Br$). Anal. ($C_{12}H_{17}Br_3N_2O_2$) C,H,N,Br.

COMPOUND 3

N,N-Bis(2-chloropropyl)-N-methyl-N-(2-nitrobenzyl) ammonium chloride (3). In a similar reaction to compound 1 2-nitrobenzyl chloride was reacted with N-methylbis(2-hydroxypropylamine) to give the diol N,N-bis(2-hydroxypropyl)-N-methyl-N-(2-nitrobenzyl)ammonium chloride as a white solid (36%) consisting of a mixture of diastereoisomers (ca. 2:1 ratio by 1H NMR): mp 193°–194° C. ($^iPrOH$). Anal. ($C_{14}H_{23}ClN_2O_4$) C, H, N, Cl. Trituration of this isomeric mixture with boiling $^iPrOH$ left a white powdery solid (overall yield ca. 6%) consisting largely of a single diastereoisomer (>95%); mp 198°–199° C.; $^1H$ NMR [$(CD_3)_2SO$] δ 8.13 (dd, J=7.9, 1.4 Hz, 1H, H-3), 7.94 (dd, J=7.6, 1.6 Hz, 1H, H-6), 7.89 (td, J=7.5, 1.5 Hz, 1H, H-4 or H-5), 7.83 (td, J=7.6, 1.6 Hz, 1H, H-4 or H-5), 5.46 (d, J=5.3 Hz, 2H, 2×OH), 5.11 (s, 2H, $ArCH_2N$), 4.46–4.33 (m, 2H, CHOH), 3.52 (d,J=13.4 Hz, 2H, $NCH_AH_BCHOH$), 3.19 (dd, J=13.4, 9.4 Hz, 2H, $NCH_AH_BCHOH$), 2.99 (s, 3H, $NCH_3$) 1.09 (d, J=6.3 Hz, 6H, $CHCH_3$); $^{13}C$ NMR [$(CD_3)_2SO$]δ 151.2 (C-2), 136.5, 133.6, 132.3, 125.7 (C-3,4,5,6), 121.0 (C-1), 67.5, 61.6 ($ArCH_2NCH_2$), 61.0 (CHOH), 48.9 ($NCH_3$), 22.1 ($CHCH_3$).

Reaction of the less soluble diol diastereoisomer with $SOCl_2$ gave N,N-bis(2-chloropropyl)-N-methyl-N-(2-nitrobenzyl)ammonium chloride (3) as pale yellow crystals (50%): mp 147°–148° C. (after two recrystallizations from ⁱPrOH-Et₂O); ¹H NMR [(CD₃)₂SO] δ8.20 (dd, J=7.2, 2.2 Hz, 1H, H-3 or 6), 8.04 (dd, J=7.0, 2.2 Hz, 1 H, H-3 or 6), 7.97–7.82 (m, 2H, H-4,5), 5.27 (s, 2H, ArCH₂N), 5.11 (pentet, J=7 Hz, 2H, CHCl), 4.19 (d, J=14.8 Hz, 2H, NCH$_A$H$_B$CHCl), 3.88 (dd, J=14.8, 8.1 Hz, 2H, NCH$_A$H$_B$CHCl), 3.16 (s, 3H, NCH₃), 1.59 (d, J=6.6 Hz, 6H, CHCH₃); ¹³C NMR [(CD₃)₂SO] δ 150.8 (C-2), 136.6, 133.9, 132.6, 126.1 (C-3,4,5,6), 120.4 (C-1), 68.3, 61.6 (ArCH₂NCH₂), 50.5, 48.0 (NCH₃, CHCH₃), 24.4 (CHCH₃). Anal. (C₁₄H₂₁Cl₃N₂O₂.H₂O) C,H,N.

COMPOUND 4

N,N-Bis(2-chloroethyl)-N-methyl-N-(3-nitrobenzyl) ammonium chloride (4). By similar reaction to compound 1, 3-nitrobenzyl chloride was reacted with N-methyldiethanolamine to give the diol N,N-bis(2-hydroxyethyl)-N-methyl-N-(3-nitrobenzyl)ammonium chloride as a cream solid (77%): mp 130°–131° C. (EtOH); ¹H NMR [(CD₃)₂SO] δ 8.61 (t, J=1.6 Hz, 1H, H-2), 8.38 (dd, J=8.0, 1.8 Hz, 1H, H-4 or H-6), 8.17 (d, J=7.8 Hz, 1H, H-4 or H-6), 7.82 (t, J=8.0 Hz, 1H, H-5), 5.68 (t, J=5.0 Hz, 2 H, 2×OH), 4.95 (s, 2H, ArCH₂N), 4.00–3.88 (m, 4H, NCH₂CH₂O), 3.67–3.59 (m, 2H, NCH₂CH₂O), 3.48–3.40 (m, 2H, NCH₂CH₂O), 3.10 (s, 3H, NCH₃); ¹³C NMR [(CD₃)₂SO] δ 147.9 (C-3), 139.9, 130.3, 128.2, 124.9 (C-2, 4,5,6), 130.1 (C-1), 64.8, 62.9 (ArCH₂NCH₂), 54.7 (CH₂OH), 48.1 (NCH₃). Anal. (Cl₁₂H₁₉ClN₂O₄) C,H,N,Cl.

Reaction of the above diol with SOCl₂ gave N,N-bis(2-chloroethyl)-N-methyl-N-(3-nitrobenzyl)ammonium chloride (4) as a white microcrystalline solid (92%): mp 157°–158° C. (EtOH-Et₂O); ¹H NMR [(CD₃)₂SO] δ 8.57 (t, J=1.8 Hz, 1H, H-2), 8.44–8.39 (m, 1H, H-4 or H-6), 8.13 (d, J=7.8 Hz, 1H, H-4 or H-6), 7.85 (t, J=7.8 Hz, 1H, H-5), 5.05 (s, 2H, ArCH₂N), 4.31–4.15 (m, 4H, NCH₂CH₂Cl), 4.05–3.94 (m, 2H, NCH₂CH₂Cl), 3.83–3.71 (m, 2H, NCH₂CH₂Cl), 3.19 (s, 3H, NCH₃); ¹³C NMR [(CD₃)₂SO] δ 147.9 (C-3), 139.6, 130.5, 127.9, 125.2 (C-2,4,5,6), 129.2 (C-1), 63.9, 61.0 (ArCH₂NCH₂), 47.2 (NCH₃), 36.0 (CH₂Cl). Anal. (Cl₂H₁₇Cl₃N₂O₂.H₂O) C,H,N,Cl.

COMPOUND 5

N,N-Bis(2-chloroethyl)-N-methyl-N-(4-nitrobenzyl) ammonium chloride (5). By similar reaction to Compound 14-nitrobenzyl chloride was reacted with N-methyldiethanolamine to give the diol N,N-bis(2-hydroxyethyl)-N-methyl-N-(4-nitrobenzyl)ammonium chloride as hygroscopic white needles (56%): mp 96°–97° C. (ⁱPrOH); ¹H NMR [(CD₃)₂SO] δ 8.34 (d, J=8.6 Hz, 2H, H-3,5), 8.01 (d, J=8.6 Hz, 2H, H-2,6), 5.69 (t, J=5.1 Hz, 2×OH), 4.94 (s, 2H, ArCH₂N), 4.00–3.90 (m, 4H, NCH₂CH₂O), 3.68–3.58 (m, 2H, NCH₂CH₂O), 3.48–3.39 (m, 2H, NCH₂CH₂O), 3.10 (s, 3H, NCH₃); ¹³C NMR [(CD₃)₂SO] δ 148.4 (C-4), 135.3 (C-1), 134.9, 123.5 (C-2 and 6, 3 and 5), 64.6, 63.0 (ArCH₂NCH₂), 54.7 (CH₂OH), 48.2 (NCH₃). Anal. (Cl₂H₁₉ClN₂O₄.2H₂O) C,H,N.

Reaction of the above diol with SOCl₂ gave N,N-bis(2-chloroethyl)-N-methyl-N-(4-nitrobenzyl)ammonium chloride (5) as a white powder (45%): mp 175°–177° C. (EtOH/Et₂O; then ground and dried 90° C./1 mmHg to remove EtOH of crystallization); ¹H NMR [(CD₃)₂SO] δ58.37 (d, J=8.7 Hz, 2 It H-3,5), 7.97 (d, J=8.7 Hz, 2H, H-2,6), 5.06 (s, 2H, ArCH₂N), 4.31–4.16 (m, 4H, NCH₂CH₂Cl), 4.04–3.94 (m, 2H, NCH₂CH₂Cl), 3.81–3.71 (m, 2H, NCH₂CH₂Cl), 3.20 (s, 3H, NCH₃); ¹³C NMR [(CD₃)₂SO] δ 148.6 (C-4), 134.7, 123.7 (C-2 and 6, 3 and 5), 134.4 (C-1), 63.8, 61.1 (ArCH₂NCH₂), 47.3 (NCH₃), 36.0 (CH₂Cl). Anal. (C₁₂H₁₇C₁₃N₂O₂) C,H,N,Cl.

COMPOUND 6

N,N-Bis(2-chloroethyl)-N-methyl-N-(3-methyl-2-nitrobenzyl)ammonium chloride (6). By similar reaction to compound 13-methyl-2-nitrobenzyl chloride was reacted with N-methyldiethanolamine to give the diol N,N-bis(2-hydroxyethyl)-N-methyl-N-(3-methyl-2-nitrobenzyl) ammonium chloride as a white solid (89%): mp 120°–121° C.; ¹H NMR [(CD₃)₂SO] δ 7.85 (dd, J=6.9, 2.0 Hz, 1H, H-4 or 6), 7.73–7.66 (m, 2H, H-4 or 6 and H-5), 5.63 (t, J=5.0 Hz, 2H, 2×OH), 4.86 (s, 2H, ArCH₂N), 3.91–3.84 (m, 4H, NCH₂CH₂O), 3.66–3.58 (m, 2H, NCH₂CH₂O), 3.46–3.38 (m, 2H, NCH₂CH₂₀), 3.03 (s, 3H, NCH₃), 2.33 (s, 3H, ArCH₃); ¹³C NMR [(CD₃)₂SO] δ 152.6 (C-2), 134.2, 133.2, 131.0 (C-4,5,6), 130.4 (C-1), 119.3 (C-3), 63.4, 61.5 (ArCH₂NCH₂), 54.8 (CH₂OH), 47.9 (NCH₃), 17.0 (ArCH₃). Anal. (C₁₃H₂₁ClN₂O₄) C,H,N,Cl.

Reaction of the above diol with SOCl₂ gave N,N-bis(2-chloroethyl)-N-methyl-N-(3-methyl-2-nitrobenzyl) ammonium chloride (6) as white plates (66%): mp 167°–168° C. (ⁱPrOH); 1H NMR [(CD₃)₂SO] d 7.81 (dd, J=7.1, 1.9 Hz, 1H, H-4 or 6), 7.76–7.69 (m, 2H, H-4 or 6 and H-5), 4.86 (s, 2H, ArCH₂N), 4.22–4.09 (m, 4H, NCH₂CH₂Cl), 3.94–3.85 (m, 2H, NCH₂CH₂Cl), 3.80–3.72 (m, 2H, NCH₂CH₂Cl), 3.14 (s, 3H, NCH₃), 2.33 (s, 3H, ArCH₃); ¹³C NMR [(CD₃)₂SO] d 152.5 (C-2), 134.6, 133.3, 131.0 (C-4,5,6), 130.6 (C-1), 118.4 (C-3), 61.3, 61.0 (ArCH₂NCH₂), 47.1 (NCH₃), 35.9 (CH₂Cl), 17.0 (ArCH₃). Anal. (C₁₃H₁₉Cl₃N₂O₂) C,H,N.

COMPOUND 7

N,N-Bis(2-chloroethyl)-N-methyl-N-(4-methyl-2-nitrobenzyl)ammonium chloride (7). By similar reaction to compound 14-methyl-2-nitrobenzyl chloride was reacted with N-methyldiethanolamine to give the diol N,N-bis(2-hydroxyethyl)-N-methyl-N-(4-methyl-2-nitrobenzyl) ammonium chloride as an off-white solid (86%): mp 131°–132° C.; ¹H NMR [(CD₃)₂SO] δ 8.00 (s, 1 H, H-3), 7.90 (d, J=7.9 Hz, 1H, H-6), 7.71 (br d, J=8 Hz, 1H, H-5), 5.60 (t, J=5.0 Hz, 2H, 2×OH), 5.10 (s, 2H, ArCH₂N), 3.98–3.81 (m, 4H, NCH₂CH₂O), 3.71–3.55 (m, 2H, NCH₂CH₂O), 3.47–3.33 (m, 2H, NCH₂CH₂O), 3.00 (s, 3H, NCH₃), 2.47 (s, 3H, ArCH₃); ¹³C NMR [(CD₃)₂SO] δ 150.8 (C-2), 142.8 (C-1), 136.2, 134.0 125.7 (C-3,5,6), 118.2 (C-4), 63.3, 61.3 (ArCH₂NCH₂), 54.8 (CH₂OH), 47.6 (NCH₃), 20.4 (ArCH₃). Anal. (C₁₃H₂₁ClN₂O₄) C,H,N.

Reaction of the above diol with SOCl₂ gave N,N-bis(2-chloroethyl)-N-methyl-N-(4-methyl-2-nitrobenzyl) ammonium chloride (7) as a very pale yellow crystalline solid (73%): mp 151°–152° C. (ⁱPrOH); ¹H NMR [(CD₃)₂SO] δ 8.02 (s, 1 H, H-3), 7.92 (d, J=7.9 Hz, 1H, H-6), 7.73 (d, J=7.9 Hz, 1H, H-5), 5.15 (s, 2H, ArCH₂N), 4.28–4.16 (m, 4H, NCH₂CH₂Cl), 4.01–3.85 (m, 2H, NCH₂CH₂Cl), 3.83–3.66 (m, 2H, NCH₂CH₂Cl), 3.11 (s, 3H, NCH₃), 2.48 (s, 3H, ArCH₃); ¹³C NMR [(CD₃)₂SO] δ 150.6 (C-2), 143.2 (C-1), 136.3, 134.2, 125.9 (C-3,5,6), 117.4 (C-4), 61.2, 60.9 (ArCH₂NCH₂), 46.9 (NCH₃), 36.0 (CH₂Cl), 20.4 (ArCH₃). Anal. (C₁₃H₁₉Cl3N₂O₂) C,H,N,Cl.

COMPOUND 8

N,N-Bis(2-chloroethyl)-N-methyl-N-(5-methyl-2-nitrobenzyl)ammonium chloride (8). By similar reaction to compound 15-methyl-2-nitrobenzyl chloride was reacted with N-methyldiethanolamine to give the diol N,N-bis(2-hydroxyethyl)-N-methyl-N-(5-methyl-2-nitrobenzyl) ammonium chloride as a pale yellow-orange oil (90%): ¹H NMR [(CD$_3$)$_2$SO] δ 8.08 (d, J=8.3 Hz, 1H, H-3), 7.82 (d, J=1.3 Hz, 1H, H-6), 7.64 (dd, J=8.3, 1.3 Hz, 1H, H-4), 5.61 (t, J=5.1 Hz, 2H, 2×OH), 5.13 (s, 2H, ArCH$_2$N), 3.95–3.84 (m, 4H, NCH$_2$CH$_2$O), 3.70–3.62 (m, 2H, NCH$_2$CH$_2$O), 3.46–3.38 (m, 2H, NCH$_2$CH$_2$O), 3.01 (s, 3H, NCH$_3$), 2.48 (s, 3H, ArCH$_3$); $^{13}$C NMR [(CD$_3$)$_2$SO] δ 148.5, 144.7 (C-1,2), 136.9, 132.3, 125.9 (C-3,4,6), 121.4 (C-5), 63.6, 61.6 (ArCH$_2$NCH$_2$), 54.8 (CH$_2$OH), 47.8 (NCH$_3$), 20.8 (ArCH$_3$). MS (FAB) m/z 269 (100%, M$^+$ for ammonium ion); HRMS calcd. for C$_{13}$H$_{21}$N$_2$O$_4$ 269.1501, found 269.1476.

Reaction of the above diol with SOCl$_2$ gave N,N-bis(2-chloroethyl)-N-methyl-N-(5-methyl-2-nitrobenzyl) ammonium chloride (8) as a pale yellow crystalline solid (51%): mp 133°–134° C. (CH$_3$CN); $^1$H NMR [(CD$_3$)$_2$SO] δ 8.12 (d, J=8.4 Hz, 1H, H-3), 7.82 (d, J=1.2 Hz, 1H, H-6), 7.67 (dd, J=8.4, 1.2 Hz, 1H, H-4), 5.17 (s, 2H, ArCH$_2$N), 4.25–4.10 (m, 4H, NCH$_2$CH$_2$Cl), 3.98–3.90 (m, 2H, NCH$_2$CH$_2$Cl), 3.82–3.73 (m, 2H, NCH$_2$CH$_2$Cl), 3.12 (s, 3H, NCH$_3$), 2.48 (s, 3H, ArCH$_3$); $^{13}$C NMR [(CD$_3$)$_2$SO] δ 148.3, 144.8 (C-1,2), 137.0, 132.7 126.1 (C-3,4,6), 120.6 (c-5), 61.4, 61.2 (ArCH$_2$NCH$_2$), 47.1 (NCH$_3$), 36.0 (CH$_2$Cl), 20.8 (ArCH$_3$). Anal. (C$_{13}$H$_{19}$Cl$_3$N$_2$O$_2$) C,H,N.

COMPOUND 9

N,N-Bis(2-chloroethyl)-N-(3-methoxy-2-nitrobenzyl)-N-methylammonium chloride (9). By similar reaction to compound 1 3-methoxy-2-nitrobenzyl chloride was reacted with N-methyldiethanolamine to give the diol N,,N-bis(2-hydroxyethyl)-N-(3-methoxy-2-nitrobenzyl)-N-methylammonium chloride as a cream solid (89%): mp 144°–145° C. (EtOH-Et$_2$O); $^1$H NMR [(CD$_3$)$_2$SO] δ 7.71 (t, J=8.2 Hz, 1H, H-5), 7.56 (d, J=8.0 Hz, 1H, H-4 or 6), 7.50 (d, J=7.2 Hz, 1H, H-4 or 6), 5.62 (t, J=5.0 Hz, 2H, 2×OH), 4.80 (s, 2H, ArCH$_2$N), 3.91 (s, 3H, OCH$_3$), 4.18–4.12 (m, 4H, NCH$_2$CH$_2$O), 3.94–3.86 (m, 2H, NCH$_2$CH$_2$O), 3.76–3.68 (m, 2H, NCH$_2$CH$_2$O), 3.02 (s, 3H, NCH$_3$); $^{13}$C NMR [(CD$_3$)$_2$SO] δ 150.7 (C-2), 142.7 (C-1), 132.1, 126.2, 116.2 (C-4,5,6), 120.4 (C-3), 63.5, 61.3 (ArCH$_2$NCH$_2$), 57.0 (OCH$_3$), 54.9 (CH$_2$OH), 48.1 (NCH$_3$). Anal. (C$_{13}$H$_{21}$ClN$_2$O$_5$) C,H,N,Cl.

Reaction of the above diol with SOCl$_2$ gave N,N-bis(2-chloroethyl)-N-(3-methoxy-2-nitrobenzyl)-N-methylammonium chloride (9) as pale yellow crystals (72%): mp 175°–176° C. ($^i$PrOH); $^1$H NMR [(CD$_3$)$_2$SO] δ 7.73 (t, J=8.2 Hz, 1H, H-5), 7.59 (d, J=8.6 Hz, 1H, H-4 or H-6), 7.50 (d, J=7.8 Hz, 1H, H-4 or 6), 4.86 (s, 2H, ArCH$_2$N), 4.22–4.08 (m, 4H, NCH$_2$CH$_2$Cl), 3.92 (s, 3H, OCH$_3$), 3.98–3.86 (m, 2H, NCH$_2$CH$_2$Cl), 3.82–3.73 (m, 2H, NCH$_2$CH$_2$Cl), 3.16 (s, 3H, NCH$_3$); $^{13}$C NMR [(CD$_3$)$_2$SO] δ 150.8 (C-2), 142.6 (C-1), 132.1, 126.3, 119.5, 116.5 (C-3,4,5,6), 61.5, 60.7 (ArCH$_2$NCH$_2$), 57.1 (OCH$_3$), 47.3 (NCH$_3$), 36.1 (CH$_2$Cl). Anal. (C$_{13}$H$_{19}$Cl$_3$N$_2$O$_3$) C,H,N.

COMPOUND 10

N,N-Bis(2-chloroethyl)-N-(4-methoxy-2-nitrobenzyl)-N-methylammonium chloride (10). By similar reaction to compound 1 4-methoxy-2-nitrobenzyl chloride was reacted with N-methyldiethanolamine to give the diol N,N-bis(2-hydroxyethyl)-N-(4-methoxy-2-nitrobenzyl)-N-methylammonium chloride as a cream crystalline solid (78%): mp 142°–143° C. ($^i$PrOH); $^1$H NMR [(CD$_3$)$_2$SO] δ 7.93 (d, J=8.7 Hz, 1H, H-6), 7.68 (d, J=2.7 Hz, 1H, H-3), 7.45 (dd, J=8.7, 2.7 Hz, 1H, H-5), 5.59 (t, J=5.0 Hz, 2H, 2×OH), 5.04 (s, 2H, ArCH$_2$N), 3.92 (s, 3H, OCH$_3$), 3.91–3.83 (m, 4H, NCH$_2$CH$_2$O), 3.64–3.55 (m, 2H, NCH$_2$CH$_2$O), 3.41–3.33 (m, 2H, NCH$_2$CH$_2$O), 2.97 (s, 3H, NCH$_3$); $^{13}$C NMR [(CD$_3$)$_2$SO] δ 161.0, 152.1 (C-1,2), 137.6, 118.9, 111.0 (C-3,5,6), 112.5 (C-4), 63.1, 61.3 (ArCH$_2$NCH$_2$), 56.3 (OCH$_3$), 54.8 (CH$_2$OH), 47.4 (NCH$_3$). Anal. (C$_{13}$H$_{21}$ClN$_2$O$_5$) C,H,N,Cl.

Reaction of the above diol with SOCl$_2$ gave N,N-bis(2-chloroethyl)-N-(4-methoxy-2-nitrobenzyl)-N-methylammonium chloride (10) as pale yellow prisms (34%): mp 142°–143° C. ($^i$PrOH-EtOAc); $^1$H NMR [(CD$_3$)$_2$SO] δ 7.89 (d, J=8.7 Hz, 1H, H-6), 7.70 (d, J=2.8 Hz, 1H, H-3), 7.48 (dd, J=8.7, 2.8 Hz, 1H, H-5), 5.05 (s, 2H, ArCH$_2$N), 4.21–4.07 (m, 4H, NCH$_2$CH$_2$Cl), 3.93–3.83 (m, 2H, NCH$_2$CH$_2$Cl), 3.92 (s, 3H, OCH$_3$), 3.76–3.67 (m, 2H, NCH$_2$CH$_2$Cl), 3.06 (s, 3H, NCH$_3$); $^{13}$C NMR [(CD$_3$)$_2$SO] δ 161.3, 152.0 (C-1,2), 137.7, 119.0, 111.2 (C-3,5,6), 111.6 (C-4), 61.0, 60.9 (ArCH$_2$NCH$_2$), 56.3 (OCH$_3$), 46.6 (NCH$_3$), 35.9 (CH$_2$Cl). Anal. (C$_{13}$H$_{19}$Cl$_3$N$_2$O$_3$) C,H,N,Cl.

COMPOUND 11

N,N-Bis(2-chloroethyl)-N-(5-methoxy-2-nitrobenzyl)-N-methylammonium chloride (11). MsCl (1.9 mL, 24 mmol) was added to Et$_3$N (4.5 mL, 32 mmol) and 5-methoxy-2-nitrobenzyl alcohol (1.48 g, 8.1 mmol) in CH$_2$Cl$_2$ (80 mL) and the mixture kept at reflux for 12 h. The solution was cooled, washed with dilute HCl (2N, 2×50 mL), dried (Na$_2$SO$_4$), concentrated, and filtered through a short column of silica (eluting with 9:1 petroleum ether:EtOAc) to give 5-methoxy-2-nitrobenzyl chloride as a yellow liquid (1.55 g, 95%). $^1$H NMR (CDCl$_3$) δ 8.17 (d, J=9.1 Hz, 1H, H-3), 7.20 (d, J=2.8 Hz, 1H, H-6), 6.93 (dd, J=9.1, 2.8 Hz, 1H, H-4), 5.03 (s, 2H, ArCH$_2$Cl), 3.93 (s, 3H, ArOCH$_3$); $^{13}$C NMR (CDCl$_3$) δ 163.7 (C-2), 140.7, 135.5, 128.2, 116.5, 113.7 (C-1,3,4,5,6), 56.1 (OCH$_3$), 43.7 (CH$_2$Cl); MS (EI) m/z 201 [70%, M$^+$ ($^{35}$Cl)], 184 (100%), 166 (60%, M—Cl), 156 (50%), 106 (70%); HRMS (EI) Calcd. for C$_8$H$_8$ClNO$_3$ 203.0163 ($^{35}$Cl). Found 203.0165.

Reaction of this chloride with N-methyldiethanolamine gave the diol N,,N-bis(2-hydroxyethyl)-N-(5-methoxy-2-nitrobenzyl)-N-methylammonium chloride as light orange prisms (73%): mp 143°–144° C. ($^i$PrOH); $^1$H NMR [(CD$_3$)$_2$SO] δ 8.24 (d, J=9.2 Hz, 1H, H-3), 7.60 (d, J=2.8 Hz, 1H, H-6), 7.34 (dd, J=9.2, 2.8 Hz, 1H, H-4), 5.60 (t, J=5.1 Hz, 2H, 2×OH), 5.20 (s, 2H, ArCH$_2$N), 3.95 (s, 3H, OCH$_3$), 3.93–3.85 (m, 4H, NCH$_2$CH$_2$O), 3.72–3.64 (m, 2H, NCH$_2$CH$_2$O), 3.47–3.40 (m, 2H, NCH$_2$CH$_2$O), 3.03 (s, 3H, NCH$_3$); $^{13}$C NMR [(CD$_3$)$_2$SO] δ 162.6 (C-2), 143.2 (C-1), 128.8, 122.2, 116.2 (C-3,4,6), 124.4 (C-5), 63.7, 61.8 (ArCH$_2$NCH$_2$), 56.4 (OCH$_3$), 54.8 (CH$_2$OH), 47.7 (NCH$_3$). Anal. (C$_{13}$H$_{21}$ClN$_2$O$_5$) C,H,N,Cl.

Reaction of the above diol with SOCl$_2$ gave N,N-bis(2-chloroethyl)-N-(5-methoxy-2-nitrobenzyl)-N-methylammonium chloride (11) as pale yellow-brown prisms (47%): mp 126°–127° C. ($^i$PrOH-EtOAc); $^1$H NMR [(CD$_3$)$_2$SO] δ 8.25 (d, J=9.2 Hz, 1H, H-3), 7.69 (d, J≦2.8 Hz, 1H, H-6), 7.37 (dd, J=9.2, 2.8 Hz, 1H, H-4), 5.27 (s, 2H, ArCH$_2$N), 4.26–4.11 (m, 4H, NCH$_2$CH$_2$Cl), 4.03–3.93 (m, 2H, NCH$_2$CH$_2$Cl), 3.96 (s, 3H, OCH$_3$), 3.84–3.75 (m, 2H, NCH$_2$CH$_2$Cl), 3.16 (s, 3H, NCH$_3$); $^{13}$C NMR [(CD$_3$)$_2$SO]δ 162.7 (C-2), 143.0 (C-1), 129.0, 122.4, 116.6 (C-3,4,6), 123.6 (C-5), 61.5, 61.4 (ArCH$_2$NCH$_2$), 56.6 (OCH$_3$), 47.1 (NCH$_3$), 36.1 (CH$_2$Cl). Anal. (C$_{13}$H$_{19}$C$_{13}$N$_2$O$_3$.0.5H$_2$O) C,H,N.

COMPOUND 12

N,N-Bis(2-chloroethyl)-N-(3,5-dinitrobenzyl)-N-methylammonium chloride (12). By similar reaction to compound 13,5-dinitrobenzyl chloride was reacted with N-methyldiethanolamine to give the diol N-(3,5-dinitrobenzyl)-N,N-bis(2-hydroxyethyl)-N-methylammonium chloride as hygroscopic pink needles (57%): mp 206°–207° C. (EtOH); $^1$H NMR [(CD$_3$)$_2$SO] δ 9.05 (d, J=2.1 Hz, 2H, H-2,6), 8.94 (t, J=2.1 Hz, 1H, H-4), 5.71 (t, J=5.0 Hz, 2H, 2×OH), 5.08 (s, 2H, ArCH$_2$N), 4.01–3.87 (m, 4H, NCH$_2$CH$_2$O), 3.71–3.62 (m, 2H, NCH$_2$CH$_2$O), 3.52–3.43 (m, 2H, NCH$_2$CH$_2$O), 3.14 (s, 3H, NCH$_3$); $^{13}$C NMR [(CD$_3$)$_2$SO] δ 148.2 (C-3,5), 134.0 (C-2, 6), 132.0 (C-1), 119.9 (C-4), 63.8, 63.2 (ArCH$_2$NCH$_2$), 54.8 (CH$_2$OH), 48.1 (NCH$_3$). Anal. (C$_{12}$H$_{18}$ClN$_3$O$_6$) C,H,N,Cl.

Reaction of the above diol with SOCl$_2$ gave N,N-bis(2-chloroethyl)-N-(3,5-dinitrobenzyl)-N-methylammonium chloride (12) as white needles (84%): mp 201°–202° C. (EtOH); $^1$H NMR [(CD$_3$)$_2$SO] δ 8.98–8.95 (m, 3H, H-2,4,6), 5.10 (s, 2H, ArCH$_2$N), 4.29–4.14 (m, 4H, NCH$_2$CH$_2$Cl), 4.06–3.97 (m, 2H, NCH$_2$CH$_2$Cl), 3.83–3.75 (m, 2H, NCH$_2$CH$_2$Cl), 3.21 (s, 3H, NCH$_3$); $^{13}$C NMR [(CD$_3$)$_2$SO] δ 148.3 (C-3,5), 133.7 (C-2,6), 130.8 (C-1), 120.2 (C-4), 63.2, 61.4 (ArCH$_2$NCH$_2$), 47.2 (NCH$_3$), 35.9 (CH$_2$Cl). Anal. (Cl$_2$H$_{16}$Cl$_3$N$_3$O$_4$) C,H,N,Cl.

COMPOUND 13

N,N-Bis(2-chloroethyl)-N-methyl-N-[(4-methylsulfonyl)benzyl]ammonium chloride (13). By similar reaction to compound 14-methylsulfonyl benzyl chloride was reacted with N-methyldiethanolamine to give the diol N,N-bis(2-hydroxyethyl)-N-methyl-N-[(4-methylsulfonyl)benzyl] ammonium chloride as white needles (785): mp 130°–131° C. (EtOH); $^1$H NMR [(CD$_3$)$_2$SO] δ 8.05 (d, J=8.2 Hz, 2H, H-2,6 or H-3,5), 7.96 (d, J=8.2 Hz, 2H, H-2,6 or H-3,5), 5.63 (t, J=5.1 Hz, 2H, 2×OH), 4.88 (s, 2H, ArCH$_2$N), 3.97–3.90 (m, 4H, NCH$_2$CH$_2$O), 3.64–3.56 (m, 2H, NCH$_2$CH$_2$O), 3.48–3.41 (m, 2H, NCH$_2$CH$_2$O), 3.28 (s, 3H, NCH$_3$), 3.08 (s, 3H, SO$_2$CH$_3$); $^{13}$C NMR [(CD$_3$)$_2$SO] δ 142.1 (C-4), 133.5 (C-1), 134.4, 127.1 (C-2 and 6, C-3 and 5), 65.1, 63.0 (ArCH$_2$NCH$_2$), 54.7 (CH$_2$OH), 48.2 (NCH$_3$), 43.2 (SO$_2$CH$_3$). Anal. (C$_{13}$H$_{22}$ClNO$_4$S) C,H,N.

Reaction of the above diol with SOCl$_2$ gave N,N-bis(2-chloroethyl)-N-methyl-N-[(4-methylsulfonyl)benzyl] ammonium chloride (13) as a white crystalline solid (55%): mp 179°–180° C. ($^i$PrOH-EtOH); $^1$H NMR [(CD$_3$)$_2$SO] δ 8.08 (d, J=8.3 Hz, 2H, H-2,6 or H-3,5), 7.93 (d, J=8.3 Hz, 2H, H-2,6 or H-3,5), 5.00 (s, 2H, ArCH$_2$N), 4.29–4.16 (m, 4H, NCH$_2$CH$_2$Cl), 4.01–3.91 (m, 2H, NCH$_2$CH$_2$Cl), 3.79–3.70 (m, 2H, NCH$_2$CH$_2$Cl), 3.28 (s, 3H, NCH$_3$), 3.18 (s, 3H, SO$_2$CH$_3$); $^{13}$C NMR [(CD$_3$)$_2$SO] δ 142.4 (C-4), 132.7 (C-1), 134.2, 127.3 (C-2 and 6, C-3 and 5), 64.2, 61.1 (ArCH$_2$NCH$_2$), 47.3 (NCH$_3$), 43.2 (SO$_2$CH$_3$), 36.0 (CH$_2$Cl). Anal. (C$_{13}$H$_{20}$Cl$_3$NO$_2$S.0.5H$_2$O) C,H,N.

COMPOUND 14

N,N-Bis(2-chloroethyl)-N-methyl-N-[(5-nitro-1-naphthyl)methyl]ammonium chloride (14). By similar reaction to compound 1 5-nitro-1-naphthylmethyl chloride was reacted with N-methyldiethanolamine to give the diol N,N-bis(2-hydroxyethyl)-N-methyl-N-[(5-nitro-1-naphthyl)methyl]ammonium chloride as a pale yellow crystalline solid (78%): mp 134°–135° C. (EtOH-Et$_2$O); 1H NMR [(CD$_3$)$_2$SO] δ 9.01 (d, J=8.7 Hz, 1H, ArH), 8.42 (d, J=8.7 Hz, 1H, ArH, 8.33 (d, J=7.5 Hz, 1H, ArH, 8.17 (d, J=7.1 Hz, 1H, ArH, 7.95–7.83 (m, 2H, 2×ArH, 5.65 (t, J=5.0 Hz, 2H, 2×OH), 5.38 (s, 2H, ArCH$_2$N), 4.00–3.90 (m, 4H, NCH$_2$CH$_2$O), 3.80 (dt, J=13.5, 5.2 Hz, 2H, NCH$_2$CH$_2$O), 3.48 (dt, J=13:5, 5.2 Hz, 2H, NCH$_2$CH$_2$O), 3.05 (s, 3H, NCH$_3$); $^{13}$C NMR [(CD$_3$)$_2$SO] δ 147.5 (C-S), 135.4, 130.4, 128.5, 126.2, 125.0, 123.5 (C-2,3,4,6,7,8), 133.8, 125.6, 124.6 (C-1,9,10), 63.2, 62.9 (ArCH$_2$NCH$_2$), 55.0 (CH$_2$OH), 48.0 (NCH$_3$). Anal. (C$_{16}$H$_{21}$ClN$_2$O$_4$) C,H,N,Cl.

Reaction of the above diol with 8OCl$_2$ gave N,N-bis(2-chloroethyl)-N-methyl-N-[(5-nitro-1-naphthyl)methyl] ammonium chloride (14) as a pale yellow powder (64%): mp 152°–153.5° C. ($^i$PrOH-Et$_2$O); 1H NMR [(CD$_3$)$_2$SO] δ 9.08 (d, J=8.7 Hz, 1H, ArH, 8.44 (d, J=8.7 Hz, 1H, ArH, 8.35 (d, J=7.5 Hz, 1H, ArH, 8.13 (d, J=7.2 Hz, 1H, ArH, 7.94 (t, J=8.3 Hz, 1H, ArH, 7.87 (t, J=8.1 Hz, 1H, ArH, 5.44 (s, 2H, ArCH$_2$N), 4.32–4.24 (m, 2H, NCH$_2$CH$_2$Cl), 4.23–4.08 (m, 4H, NCH$_2$CH$_2$Cl), 3.88–3.81 (m, 2H, NCH$_2$CH$_2$Cl), 3.14 (s, 3H, NCH$_3$); $^{13}$C NMR [(CD$_3$)$_2$SO] δ 147.4 (C-5), 135.5, 130.2, 128.5, 126.1, 125.3, 123.4 (C-2,3,4,6,7,8), 133.7, 124.8, 124.6 (C-1,9,10), 62.5, 61.1 (ArCH$_2$NCH$_2$), 47.1 (NCH$_3$), 36.1 (CH$_2$Cl). Anal. (C$_{16}$H$_{19}$Cl$_3$N$_2$O$_2$) C,H,N,Cl.

COMPOUND 15

N,N-Bis(2-chloroethyl)-N-methyl-N-[(8-nitro-1-naphthyl)methyl]ammonium chloride (15). By similar reaction to compound 18-nitro-1-naphthylmethyl chloride was reacted with N-methyldiethanolamine to give the diol N,N-bis(2-hydroxyethyl)-N-methyl-N-[(8-nitro-1-naphthyl)methyl]ammonium chloride as a brown oil (70%): $^1$H NMR [(CD$_3$)$_2$SO] δ 8.47 (d, J=8.2 Hz, 1H, ArH, 8.42 (d, J=8.2 Hz, 1H, ArH, 8.25 (d, J=7.5 Hz, 1H, ArH, 8.22 (d, J=7.3 Hz, 1H, ArH), 7.88 (t, J=7.7 Hz, 1H, ArH, 7.79 (t, J=7.8 Hz, 1H, ArH), 5.54 (t, J=4.4 Hz, 2H, 2×OH), 4.97 (s, 2H, ArCH$_2$N), 3.83–3.74 (m, 4H, NCH$_2$CH$_2$O), 3.54–3.44 (m, 2H, NCH$_2$CH$_2$O), 3.29–3.10 (m, 2H, NCH$_2$CH$_2$O), 2.72 (s, 3H, NCH$_3$); $^{13}$C NMR [(CD$_3$)$_2$SO] δ 147.1 (C-8), 138.6, 134.9, 132.6, 127.1, 125.7, 125.5 (C-2,3,4,5,6,7), 135.0, 123.4, 121.0 (C-1,9,10), 65.3, 63.4 (ArCH$_2$NCH$_2$), 54.7 (CH$_2$OH), 47.6 (NCH$_3$); MS (FAB) m/z 305 (100%, M$^+$ for the ammonium ion), 186 (50%). HRMS (FAB) Calcd. for C$_{16}$H$_{21}$N$_2$O$_4$:305.1501. Found: 305.1509.

Reaction of the above diol with SOCl$_2$ gave N,N-bis(2-chloroethyl)-N-methyl-N-[(8-nitro-1-naphthyl)methyl] ammonium chloride (15) as gold-brown prisms (37%): mp 103°–104° C. (acetone), $^1$H NMR [(CD$_3$)$_2$SO]δ 8.52 (d, J=8.3 Hz, 1H, ArH), 8.46 (d, J=8.2 Hz, 1H, ArH), 8.29 (d, J=7.5 Hz, 1H, ArH), 8.24 (d, J=7.3 Hz, I H, ArH), 7.91 (t, J=7.7 Hz, 1H, ArH), 7.82 (t, J=7.8 Hz, 1H, ArH), 4.96 (s, 2H, ArCH$_2$N), 4.15–4.05 (m, 2H, NCH$_2$CH$_2$Cl), 4.01–3.92 (m, 2H, NCH$_2$CH$_2$Cl), 3.77–3.67 (m, 2H, NCH$_2$CH$_2$Cl), 3.55–3.45 (m, 2H, NCH$_2$CH$_2$Cl), 2.81 (s, 3H, NCH$_3$); $^{13}$C NMR [(CD$_3$)$_2$SO] δ 146.9 (C-8), 138.9, 135.1, 133.1, 127.2, 126.0, 125.6 (C-2,3,4,5,6,7), 135.2, 123.3, 120.1 (C-1,9,10), 65.3, 61.5 (ArCH$_2$NCH$_2$), 46.9 (NCH$_3$), 35.9 (CH$_2$Cl). Anal. (C$_{16}$H$_{19}$Cl$_3$N$_2$O$_2$.H$_2$O) C,H,N,Cl.

COMPOUND 16

N,N-Bis(2-chloroethyl)-N-methyl-N-[(1-methyl-4-nitro-5-imidazolyl)methyl]ammonium chloride (16). By similar reaction to compound 11-methyl-4-nitro-5-imidazolyl chloride was reacted with N-methyldiethanolamine to give the diol N,N-bis(2-hydroxyethyl)-N-methyl-N-[(1-methyl-4-nitro-5-imidazolyl)methyl]ammonium chloride as a cream solid (74%): mp 177°–178° C. (EtOH-Et$_2$O); $^1$H NMR [(CD$_3$)$_2$SO] δ 8.13 (s, 1H, H-2), 5.59 (t, J=4.6 Hz, 2H, 2×OH), 5.25 (br s, 2H imidCH$_2$N), 3.98–3.86 (m, 4H, NCH$_2$CH$_2$O), 3.90 (s, 3H, imidCH$_3$), 3.85–3.75 (m, 2H, NCH$_2$CH$_2$O), 3.58–3.48 (m, 2H, NCH$_2$CH$_2$O), 3.12 (s, 3H, NCH$_3$); $^{13}$C NMR [(CD$_3$)$_2$SO] δ 147.5 (C-4), 139.8 (C-2), 120.6 (C-5), 63.5, 55.4 (imidCH$_2$NCH$_2$), 55.0 (CH$_2$OH), 47.6 (NCH$_3$), 33.8 (imidCH$_3$). Anal. (C$_{10}$H$_{19}$ClN$_4$O$_4$) C,H, N,Cl.

Reaction of the above diol with SOCl$_2$ gave N,N-bis(2-chloroethyl)-N-methyl-N-[(1-methyl-4-nitro-5-imidazolyl) methyl]ammonium chloride (16) as a white solid (66%): mp 173°–176° C. (dec., MeOH); $^1$H NMR [(CD$_3$)$_2$SO] δ 8.15 (s, 1H, H-2), 5.22 (br s, 2H, imidCH$_2$N), 4.26–4.12 (m, 4H, NCH$_2$CH$_2$Cl), 4.06–3.97 (m, 2H, NCH$_2$CH$_2$Cl), 3.95–3.86 (m, 2H, NCH$_2$CH$_2$Cl), 3.89 (s, 3H, imidCH$_3$), 3.18 (s, 3H, NCH$_3$); $^{13}$C NMR [(CD$_3$)$_2$SO] δ 147.8 (C-4), 140.2 (C-2), 119.4 (C-5), 61.4, 54.9 (imidCH$_2$NCH$_2$), 47.3 (NCH$_3$), 36.0 (CH$_2$Cl), 33.8 (imidCH$_3$). Anal. (C$_{10}$H$_{17}$Cl$_3$N$_4$O$_2$) C,H,N,C.

It is clear from the data of Table 3 that the examples of the aromatic bis(2-haloethyl) and aromatic bis(2-alkylsulfonyloxyethyl) quaternary ammonium salts of general formula (I) listed in Table 3 include compounds which are active as cytotoxic agents, having the capability of being reductively activated by mammalian tumour cells. The compounds are selectively toxic to hypoxic tumour cells, and therefore useful as anticancer drugs and can be used beneficially with radiotherapy, as radiosensitising agents.

We claim:

1. Compounds of the formula I

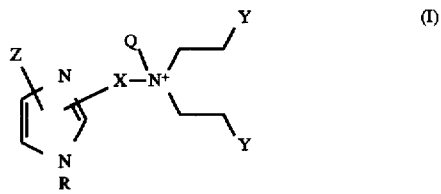
(I)

wherein X represents a linker chain —CR$_1$R$_2$— or —CR$_1$=CR$_2$— (where R$_1$ and R$_2$ are separately H, lower alkyl, phenyl or nitrophenyl); Y is halogen or OSO$_2$R; Q is lower alkyl (optionally substituted with alkyl and/or ether functions and containing up to 6 carbons) or nitrophenyl; R is lower alkyl optionally substituted with alkyl and/or ether groups, and may contain up to eight carbon atoms, Z represents one or more of the groups NO$_2$, SO$_2$R, CONHR, R, OR, SR, and CF$_3$, and the pharmaceutically acceptable salts thereof.

2. Compounds of claim 11, which are N,N-Bis(2-chloroethyl)-N-methyl-N-[(1-methyl-4-nitro-5-imidazoyl) methyl]ammonium chloride.

3. Pharmaceutical compositions comprising a compound according to claim 1 in combination with a pharmaceutically acceptable carrier or diluent.

4. A process for making compounds of the formula I

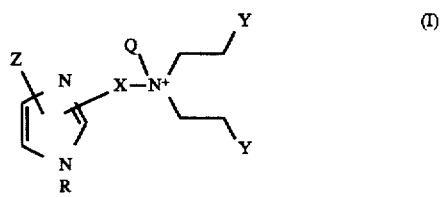
(I)

wherein X represents a linker chain —CR$_1$R$_2$— or —CR$_1$=CR$_2$— (where R$_1$ and R$_2$ are separately H, lower alkyl, phenyl or nitrophenyl); Y is halogen or OSO$_2$R; Q is lower alkyl (optionally substituted with alkyl and/or ether functions and containing up to 6 carbons) or nitrophenyl; R is lower alkyl optionally substituted with alkyl and/or ether groups, and may contain up to eight carbon atoms, Z represents one or more of the groups NO$_2$, SO$_2$R, CONHR, R, OR, SR, and CF$_3$, and the pharmaceutically acceptable salts thereof, according to the following reaction scheme:

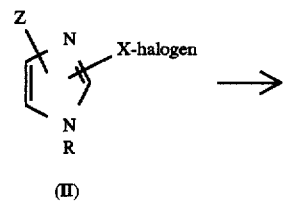
(II)

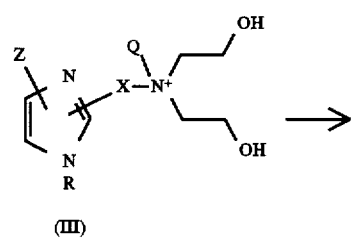
(III)

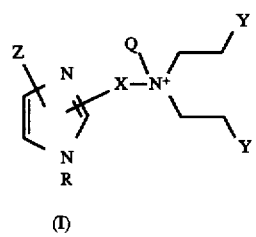
(I)

comprising reacting heteroaromatic aromatic α-methyl halides of the formula II with N-alkyl or N-aryldiethanolamines to give the quaternary diols of the formula III, and converting the quaternary diols of formula III to compounds of formula I by treatment with SOCl$_2$ at room temperature.

5. A method of treating neoplastic cells comprising administering to a patient in need of such treatment an effective amount of a compound of the formula I

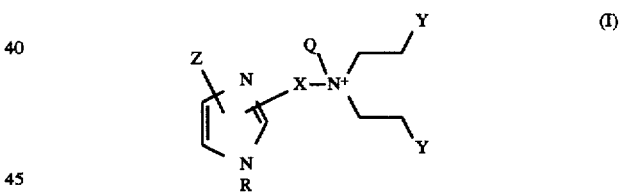
(I)

wherein X represents a linker chain —CR$_1$R$_2$— or —CR$_1$=CR$_2$— (where R$_1$ and R$_2$ are separately H, lower alkyl, phenyl or nitrophenyl); Y is halogen or OSO$_2$R; Q is lower alkyl (optionally substituted with alkyl and/or ether functions and containing up to 6 carbons) or nitrophenyl; R is lower alkyl optionally substituted with alkyl and/or ether groups, and may contain up to eight carbon atoms, Z represents one or more of the groups NO$_2$, SO$_2$R, CONHR, R, OR, SR, and CF$_3$, and the pharmaceutically acceptable salts thereof.

6. The method of claim 5, wherein the compound is N,N-Bis(2-chloroethyl)-N-methyl-N-[(1-methyl-4-nitro-5-imidazoyl)methyl]ammonium chloride.

7. The method of claim 5, further comprising conjunctively administering pharmaceuticals having an inhibitory effect on tumor blood flow and administering radiotherapy treatment.

* * * * *